United States Patent
Tzeng et al.

(10) Patent No.: US 11,314,116 B2
(45) Date of Patent: Apr. 26, 2022

(54) SENSING DISPLAY APPARATUS

(71) Applicant: Au Optronics Corporation, Hsinchu (TW)

(72) Inventors: Shu-Wen Tzeng, Changhua County (TW); Yen-Hua Lo, Taichung (TW); Chia-Chi Lee, Hsinchu (TW); Cheng-Hsiang Huang, Hsinchu (TW)

(73) Assignee: Au Optronics Corporation, Hsinchu (TW)

( * ) Notice: Subject to any disclaimer, the term of this patent is extended or adjusted under 35 U.S.C. 154(b) by 287 days.

(21) Appl. No.: 16/562,444

(22) Filed: Sep. 6, 2019

(65) Prior Publication Data

US 2020/0081286 A1    Mar. 12, 2020

(30) Foreign Application Priority Data

Sep. 6, 2018   (TW) .................. 107131348
Dec. 20, 2018  (TW) .................. 107146277

(51) Int. Cl.
*G02F 1/1333* (2006.01)
*G02F 1/1362* (2006.01)
(Continued)

(52) U.S. Cl.
CPC .......... *G02F 1/13338* (2013.01); *G02F 1/135* (2013.01); *G02F 1/1368* (2013.01);
(Continued)

(58) Field of Classification Search
CPC ................ G06F 3/0412; G06F 3/0421; G06F 2203/04103; G06K 9/00006;
(Continued)

(56) References Cited

U.S. PATENT DOCUMENTS 8,946,732 B2    2/2015  Fan et al.
10,108,839 B2  10/2018  Uehara et al.
(Continued)

FOREIGN PATENT DOCUMENTS

CN    106803514    6/2017
CN    107065358    8/2017
(Continued)

*Primary Examiner* — Hoan C Nguyen
(74) *Attorney, Agent, or Firm* — JCIPRNET

(57) ABSTRACT

A sensing display apparatus includes a pixel array substrate, a sensing device substrate, and a display medium layer. The sensing device substrate includes a first substrate, a sensing device, first to third signal lines, and a shielding layer. The sensing device includes a first switching element electrically connected with the first and second signal lines, an electrically conductive layer electrically connected with the third signal line, an electrode layer electrically connected with the first switching element and a photo-sensitive layer disposed between the electrically conductive layer and the electrode layer. The shielding layer is disposed between the first to third signal lines and the pixel array substrate. The sensing display apparatus has light transmitting regions and a light shielding region surrounding the light transmitting regions. The sensing device and the first to third signal lines are disposed in the light shielding region.

20 Claims, 15 Drawing Sheets

(51) Int. Cl.
G02F 1/135 (2006.01)
G02F 1/1368 (2006.01)

(52) U.S. Cl.
CPC .. G02F 1/136209 (2013.01); G02F 1/136286 (2013.01); *G02F 2201/121* (2013.01)

(58) Field of Classification Search
CPC ........... G02F 1/13338; G02F 1/136286; G02F 1/135; G02F 1/1368; G02F 1/136209; G02F 2201/121; G02F 1/13712; A61B 5/1172; G06V 40/12
See application file for complete search history.

(56) References Cited

U.S. PATENT DOCUMENTS

| | | |
|---|---|---|
| 2013/0270618 A1 | 10/2013 | Fan et al. |
| 2014/0022476 A1* | 1/2014 | Park ...................... G02F 1/1362 349/41 |
| 2014/0184942 A1 | 7/2014 | Bang et al. |
| 2015/0287752 A1* | 10/2015 | Yeo ....................... H01L 21/465 257/43 |
| 2015/0301383 A1* | 10/2015 | Kimura ................... G06F 3/042 349/12 |
| 2017/0372110 A1 | 12/2017 | Uehara et al. |
| 2018/0165496 A1 | 6/2018 | Cheng et al. |
| 2018/0373079 A1* | 12/2018 | Yeh .................. G02F 1/133345 |
| 2019/0018999 A1 | 1/2019 | Uehara et al. |
| 2019/0065806 A1* | 2/2019 | Cheng ................. G06K 9/0002 |
| 2019/0113817 A1 | 4/2019 | Wang |

FOREIGN PATENT DOCUMENTS

| | | | | |
|---|---|---|---|---|
| CN | 107065365 | | 8/2017 | |
| CN | 107545235 | | 1/2018 | |
| CN | 108182872 | | 6/2018 | |
| KR | 20180048333 A | * | 5/2018 | ............... G09G 5/10 |
| TW | 201344519 | | 11/2013 | |

\* cited by examiner

SENSING DISPLAY APPARATUS

CROSS REFERENCE TO RELATED APPLICATION

This application claims the priority benefits of Taiwan application serial no. 107131348, filed on Sep. 6, 2018 and Taiwan application serial no. 107146277, filed on Dec. 20, 2018. The entirety of each of the above-mentioned patent applications is hereby incorporated by reference herein and made a part of specification.

BACKGROUND

Field of the Disclosure

The disclosure relates to a sensing display apparatus, and more particularly to a sensing display apparatus having a shielding layer.

Description of Related Art

At present, in order to improve the convenience of product use, many manufacturers install sensing device in products. For example, fingerprint sensors are often included in existing mobile phones. In the existing fingerprint identification technology, the sensing device detects the light reflected by the fingerprint of finger, and the topography of the fingerprint has different intensity of reflected light, so different fingerprint patterns are distinguished by the sensing apparatus.

However, when the sensing device substrate is mounted in the display apparatus, the electric field generated by the sensing device substrate is very likely to affect the display quality of the display apparatus. For example, the liquid crystal in the liquid crystal display apparatus may rotate due to the electric field generated by the sensing device substrate, which causes occurrence of light leakage. Therefore, there is a need for a method that can solve the aforementioned problems.

SUMMARY OF THE DISCLOSURE

The present disclosure provides a sensing display apparatus capable of improving the problem that an electric field generated by a sensing device substrate affects display quality.

At least one embodiment of the disclosure provides a sensing display apparatus including a pixel array substrate, a sensing device substrate and a display medium layer. The sensing device substrate faces the pixel array substrate, and includes a first substrate, a sensing device, a first signal line, a second signal line, a third signal line, and a shielding layer. The sensing device is disposed on the first substrate. The first signal line, the second signal line, and the third signal line are disposed on the first substrate. The sensing device includes a first switching element, an electrically conductive layer, an electrode layer and a photo-sensitive layer. The first switching element is electrically connected to the first signal line and the second signal line. The electrically conductive layer is electrically connected to the third signal line. The electrode layer is electrically connected to the first switching element. The photo-sensitive layer is disposed between the electrode layer and the electrically conductive layer. The shielding layer is disposed between the first signal line and the pixel array substrate, between the second signal line and the pixel array substrate, and between the third signal line and the pixel array substrate. The sensing display apparatus has a plurality of light transmitting regions and a light shielding region surrounding the light transmitting regions. The sensing device, the first signal line, the second signal line and the third signal line are disposed in the light shielding region. The display medium layer is disposed between the pixel array substrate and the sensing device substrate.

At least one embodiment of the disclosure provides a sensing display apparatus including a pixel array substrate, a sensing device substrate and a display medium layer. The sensing device substrate faces the pixel array substrate. The display medium layer is disposed between the pixel array substrate and the sensing device substrate. The sensing device substrate includes a first substrate, a sensing device, a first signal line, a second signal line, a third signal line and a shielding layer. The sensing device is disposed on the first substrate. The first signal line, the second signal line and the third signal line are disposed on the first substrate. The sensing device includes a first switching element, an electrically conductive layer, an electrode layer and a photo-sensitive layer. The first switching element is electrically connected to the first signal line and the second signal line. The electrically conductive layer is electrically connected to the third signal line. The electrode layer is electrically connected to the first switching element. The photo-sensitive layer is disposed between the electrode layer and the electrically conductive layer. The shielding layer is disposed between the first signal line and the pixel array substrate, between the second signal line and the pixel array substrate and between the third signal line and the pixel array substrate.

Based on the above, the configuration of the shielding layer may improve the problem that the electric field generated by the sensing device substrate affects the display quality.

In order to make the aforementioned features and advantages of the disclosure more comprehensible, embodiments accompanying figures are described in detail below.

DESCRIPTION OF EMBODIMENTS

Figure 1:
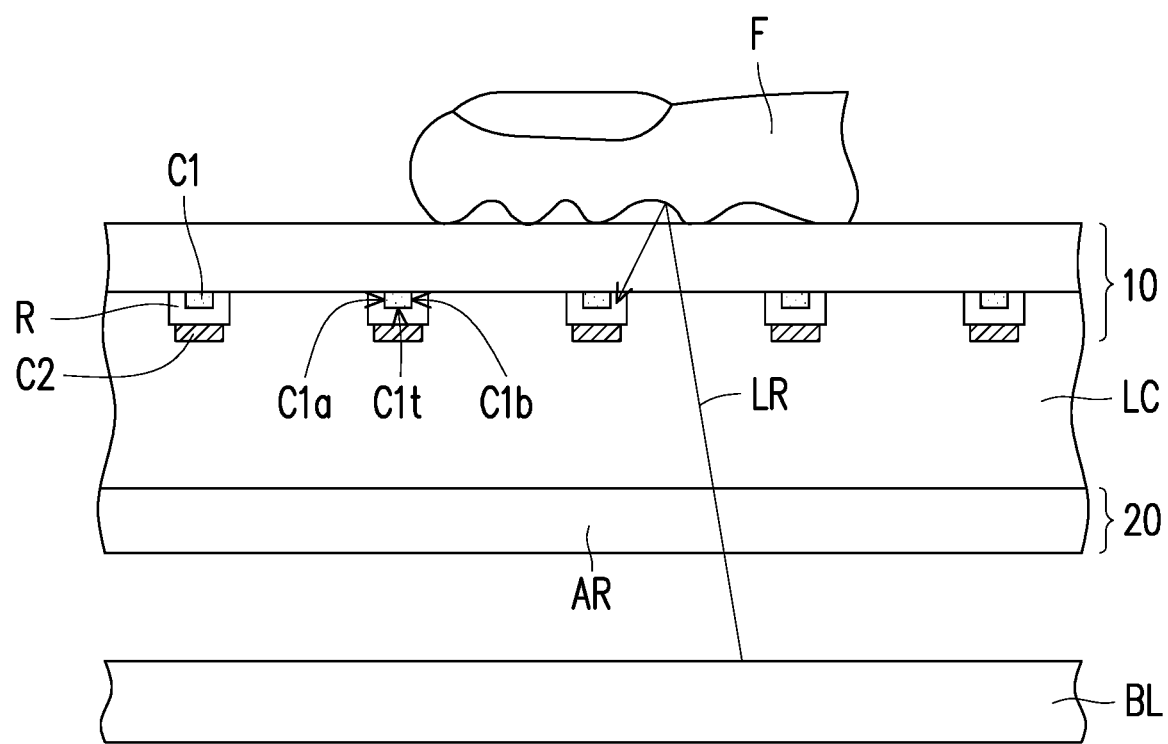
FIG. 1 is a cross-sectional view of a display apparatus according to an embodiment of the disclosure.
Figure 2:
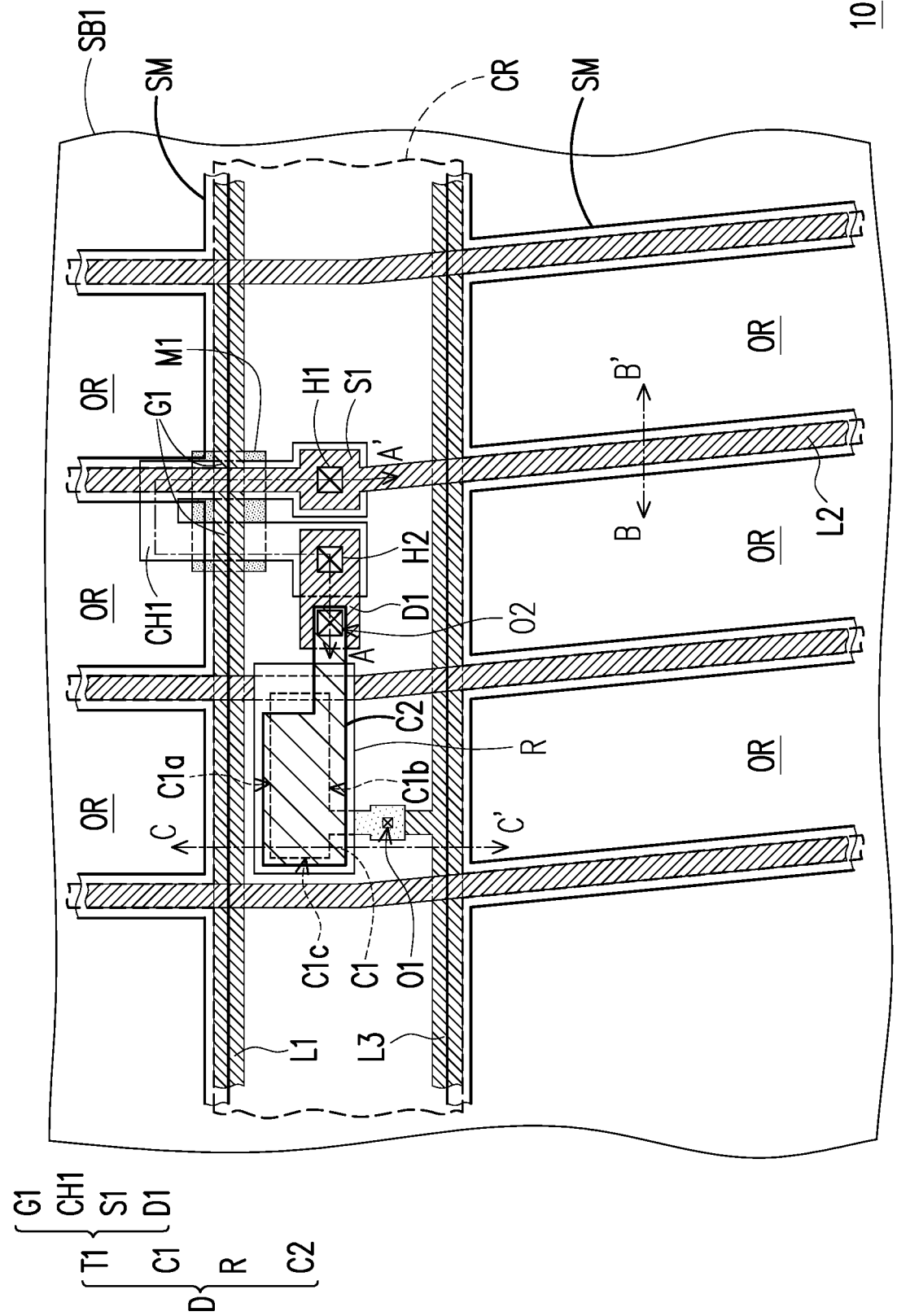
FIG. 2 is a schematic bottom view of a sensing device substrate of a display apparatus according to an embodiment of the disclosure.
Figure 3A:
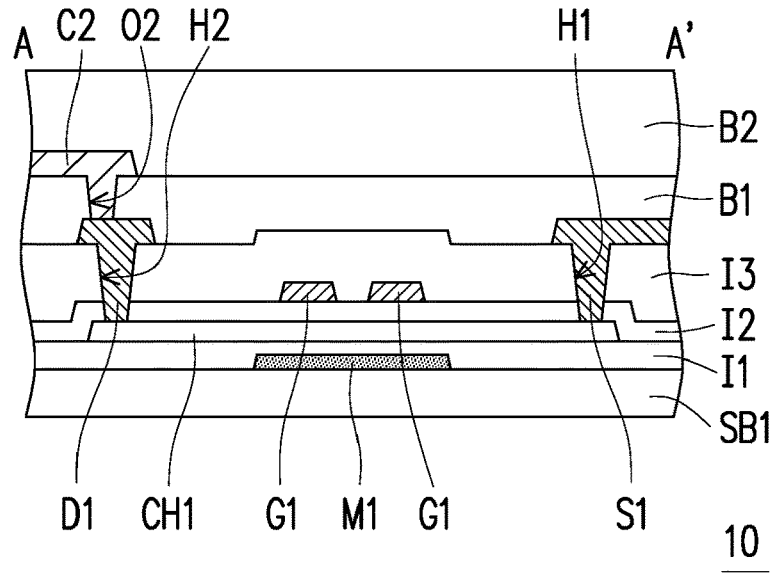
FIG. 3A is a schematic cross-sectional view of FIG. 2 taken along sectional line AA'.
Figure 3B:
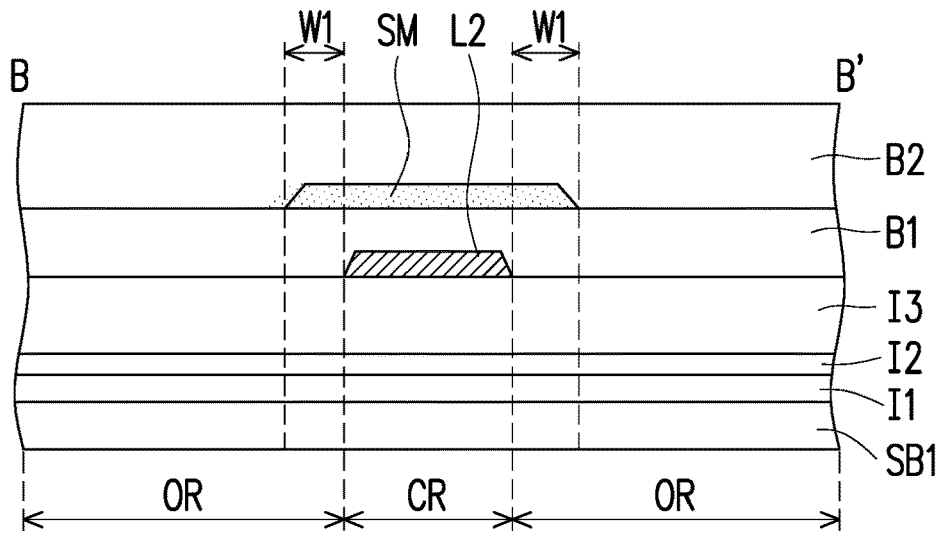
FIG. 3B is a schematic cross-sectional view of FIG. 2 taken along sectional line BB'.
Figure 3C:
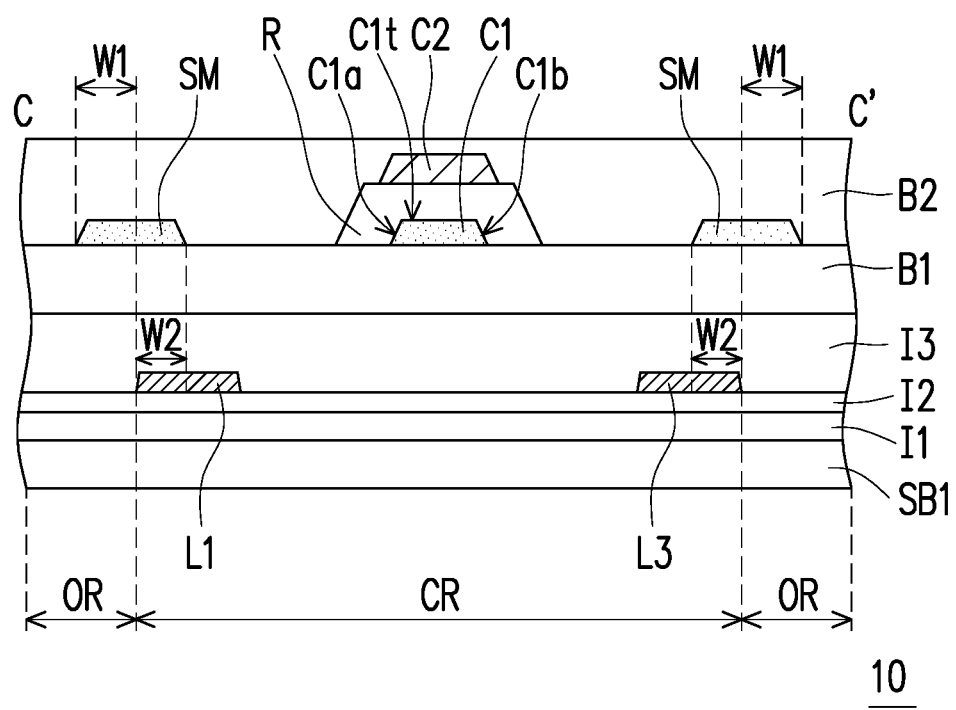
FIG. 3C is a schematic cross-sectional view of FIG. 2 taken along sectional line CC'.

FIG. 1 is a cross-sectional view of a display apparatus according to an embodiment of the disclosure. For simplicity of explanation, FIG. 1 omits some of the components of the sensing device substrate 10 and the pixel array substrate 20. FIG. 2 is a schematic bottom view of a sensing device substrate 10 of a display apparatus according to an embodiment of the disclosure. For simplicity of explanation, FIG. 2 omits illustration of some of the components in the sensing device substrate 10. FIG. 3A is a schematic cross-sectional view of FIG. 2 taken along sectional line AA'. FIG. 3B is a schematic cross-sectional view of FIG. 2 taken along sectional line BB'. FIG. 3C is a schematic cross-sectional view of FIG. 2 taken along sectional line CC'.

A sensing display apparatus 1 has a light transmitting region OR and a circuit region CR, and includes a sensing device substrate 10, a pixel array substrate 20, and a display medium layer LC. In some embodiments, the circuit region CR overlaps a black matrix (not shown), and the circuit region CR may also be referred to as a light-shielding region CR. In some embodiments, the black matrix is disposed in the sensing device substrate 10. In other embodiments, the black matrix is disposed in the pixel array substrate 20. The sensing device substrate 10 faces the pixel array substrate 20. The display medium layer LC is disposed between the pixel array substrate 20 and the sensing device substrate 10. In some embodiments, the display medium layer LC includes a negative liquid crystal, but the disclosure is not limited thereto.

Referring to FIG. 1, FIG. 2, FIG. 3A, FIG. 3B and FIG. 3C, the sensing device substrate 10 includes a first substrate SB1, a sensing device D, a first signal line L1, a second signal line L2, and a third signal line L3 and a shielding layer SM.

The material of the first substrate SB1 may be glass, quartz or an organic polymer or the like. The sensing device D is disposed on the first substrate SB1. The sensing device D, the first signal line L1, the second signal line L2, and the third signal line L3 are disposed in the circuit region CR. The first signal line L1, the second signal line L2, and the third signal line L3 are disposed on the first substrate SB1, and are electrically connected to the sensing device D.

The sensing device D includes a switching element T1, an electrically conductive layer C1, a photo-sensitive layer R, and an electrode layer C2. The switching element T1 is electrically connected to the first signal line L1 and the second signal line L2. The light shielding layer M1 is disposed between the first substrate SB1 and the switching element T1. The material of the light shielding layer M1 includes, for example, metal, resin, graphite, or other suitable materials. The light shielding layer M1 may improve the problem of light leakage generated by the switching element T1, for example. The insulating layer I1 covers the light shielding layer M1 and the first substrate SB1, and the light shielding layer M1 is disposed between the insulating layer I1 and the first substrate SB1.

In the embodiment, the switching element T1 includes a gate G1, a source S1, a drain D1, and a semiconductor channel layer CH1. The gate G1 overlaps the semiconductor channel layer CH1, and an insulating layer I2 is interposed between the gate G1 and the semiconductor channel layer CH1. The gate G1 is electrically connected to the first signal line L1. In this embodiment, the gate G1, the first signal line L1 and the third signal line L3 belong to the same conductive film layer, but the disclosure is not limited thereto. The insulating layer I3 is disposed on the insulating layer I2 and covers the gate G1. The source S1 and the drain D1 are disposed above the insulating layer I3, and the source S1 is electrically connected to the second signal line L2. In this embodiment, the source S1, the drain D1, and the second signal line L2 belong to the same conductive film layer, but the disclosure is not limited thereto. The source S1 and the drain D1 are electrically connected to the semiconductor channel layer CH1 through the openings H1 and H2 respectively, and the openings H1 and H2 are disposed, for example, in the insulating layer I3 and the insulating layer I2. The above-described switching element T1 is exemplified as a top gate type thin film transistor, but the disclosure is not limited thereto. According to other embodiments, the switching element T1 described above may also be a bottom gate type thin film transistor or other suitable thin film transistors.

The insulating layer B covers the switching element T1. The electrically conductive layer C1 is disposed on the insulating layer B1. The electrically conductive layer C1 is electrically connected to the third signal line L3. For example, the electrically conductive layer C1 is electrically connected to the third signal line L3 through the opening O1, and the opening O1 is disposed, for example, in the insulating layer B1 and the insulating layer I3. The material of the electrically conductive layer C1 is preferably a transparent conductive material, such as indium tin oxide, indium zinc oxide, aluminum tin oxide, aluminum zinc oxide, indium gallium zinc oxide or other suitable oxide or a stacked layer of at least two of the above.

The photo-sensitive layer R covers the top surface C1t of the electrically conductive layer C1, the first side surface C1a of the electrically conductive layer C1, and the second side surface C1b of the electrically conductive layer C1. In this embodiment, the electrically conductive layer C1 further has a third side surface C1c, the third side surface C1c connects the first side surface C1a and the second side surface C1b, and the photo-sensitive layer R covers the third side surface C1c of the electrically conductive layer C1. The material of the photo-sensitive layer R is, for example, a silicon-rich oxide (SRO) or other suitable material. In this embodiment, the shape of the photo-sensitive layer R vertically projected on the first substrate SB1 is a rectangle, and the long side of the photo-sensitive layer R is parallel to the first signal line L1 and the third signal line L3, but the disclosure is not limited thereto.

The electrode layer C2 covers the photo-sensitive layer R. The photo-sensitive layer R is disposed between the electrode layer C2 and the electrically conductive layer C1. The photo-sensitive layer R is disposed between the top surface C1t of the electrically conductive layer C1 and the electrode layer C2. The electrode layer C2 is farther from the first substrate SB1 than the electrically conductive layer C1. The electrode layer C2 is closer to the pixel array substrate 20 than the electrically conductive layer C1.

The electrode layer C2 is electrically connected to the switching element T1. For example, the electrode layer C2 is electrically connected to the switching element T1 through the opening O2, and the opening O2 is, for example, disposed in the insulating layer B1. The material of the electrode layer C2 is, for example, molybdenum, aluminum, titanium, copper, gold, silver or other conductive material or a stack of two or more of the above. In some embodiments, the electrode layer C2 may be used as a reflective layer, thereby increasing the light that can be received by the photo-sensitive layer R.

In some embodiments, the sensing device D may include two or more switching elements. For example, the sensing device D includes two switching elements electrically connected together and the electrically conductive layer C1, the photo-sensitive layer R and the electrode layer C2 electrically connected to the switching elements.

In the embodiment, although the third signal line L3 is electrically connected to the electrically conductive layer C1, the disclosure is not limited thereto. In other embodiments, other signal lines having the same extending direction as the first signal line L1 may also be used as the signal lines electrically connected to the electrically conductive layer C1. In some embodiments, the sensing device D is electrically connected to three or more signal lines, and the manner in which the sensing device D is connected to the signal line is not limited to the configuration illustrated in FIG. 2.

In this embodiment, the third signal line L3 and the first signal line L1 belong to the same conductive film layer, and the sensing device D is disposed between the third signal line L3 and the first signal line L1, thereby improving the area of the light transmitting region OR.

The shielding layer SM is disposed between the first signal line L1 and the pixel array substrate 20, between the second signal line L2 and the pixel array substrate 20, and between the third signal line L3 and the pixel array substrate 20. In some embodiments, the shielding layer SM and the electrically conductive layer C1 are the same conductive film layer. The shielding layer SM and the electrically conductive layer C1 are electrically connected to different signal sources.

The problem that the electric field generated by the sensing device substrate 10 affects the liquid crystal molecules in the display medium layer LC is improved by the shielding layer SM, and the display quality of the display apparatus 1 may be improved.

Referring to FIG. 3B and FIG. 3C, in the embodiment, the width W1 of the shielding layer SM extending from the circuit region CR into the light transmitting region OR is greater than or equal to 1.5 μm. For example, the shielding layer SM overlaps the first signal line L1, the second signal line L2 and the third signal line L3, and extends toward the light transmitting region OR from the first signal line L1, the second signal line L2 and the third signal line L3. The width W2 of the shielding layer SM overlapping the first signal line L1 and the third signal line L3 is greater than or equal to 1.5 μm, and the width W1 of the shielding layer SM overlapping the light transmitting region OR is greater than or equal to 1.5 μm. In this embodiment, a portion of the first signal line L1 and a portion of the third signal line L3 do not overlap the shielding layer SM. In an embodiment, the non-overlapping portion is disposed on a side closer to the electrically conductive layer C1. A portion of the first signal line L1 not overlapping the shielding layer SM is closer to the electrically conductive layer C1 than a portion of the first signal line L1 overlapping the shielding layer SM. A portion of the third signal line L3 not overlapping the shielding layer SM is closer to the electrically conductive layer C1 than a portion of the third signal line L3 overlapping the shielding layer SM. In other words, the vertical projection of the first signal line L1 and the third signal line L3 on the first substrate SB1 is deviated from the vertical projection of the shielding layer SM on the first substrate SB1. Therefore, more adequate spacing may be provided between the shielding layer SM and the electrically conductive layer C1. In the embodiment, more than 50% of the area of the light transmitting region OR does not overlap the shielding layer SM. In the embodiment, at the sectional line BB', the shielding layer SM completely overlaps the second signal line L2, and the width W1 of the shielding layer SM overlapping the light transmitting region OR is greater than or equal to 1.5 μm, wherein the shielding layer SM overlaps the second signal line L2.

In the embodiment, the sensing device substrate 10 further includes a passivation layer B2. The passivation layer B2 covers the electrically conductive layer C1, the electrode layer C2, the shielding layer SM and the insulating layer B1. The passivation layer B2 is disposed, for example, between the electrode layer C2 and the display medium layer LC (shown in FIG. 1).

Figure 4A:
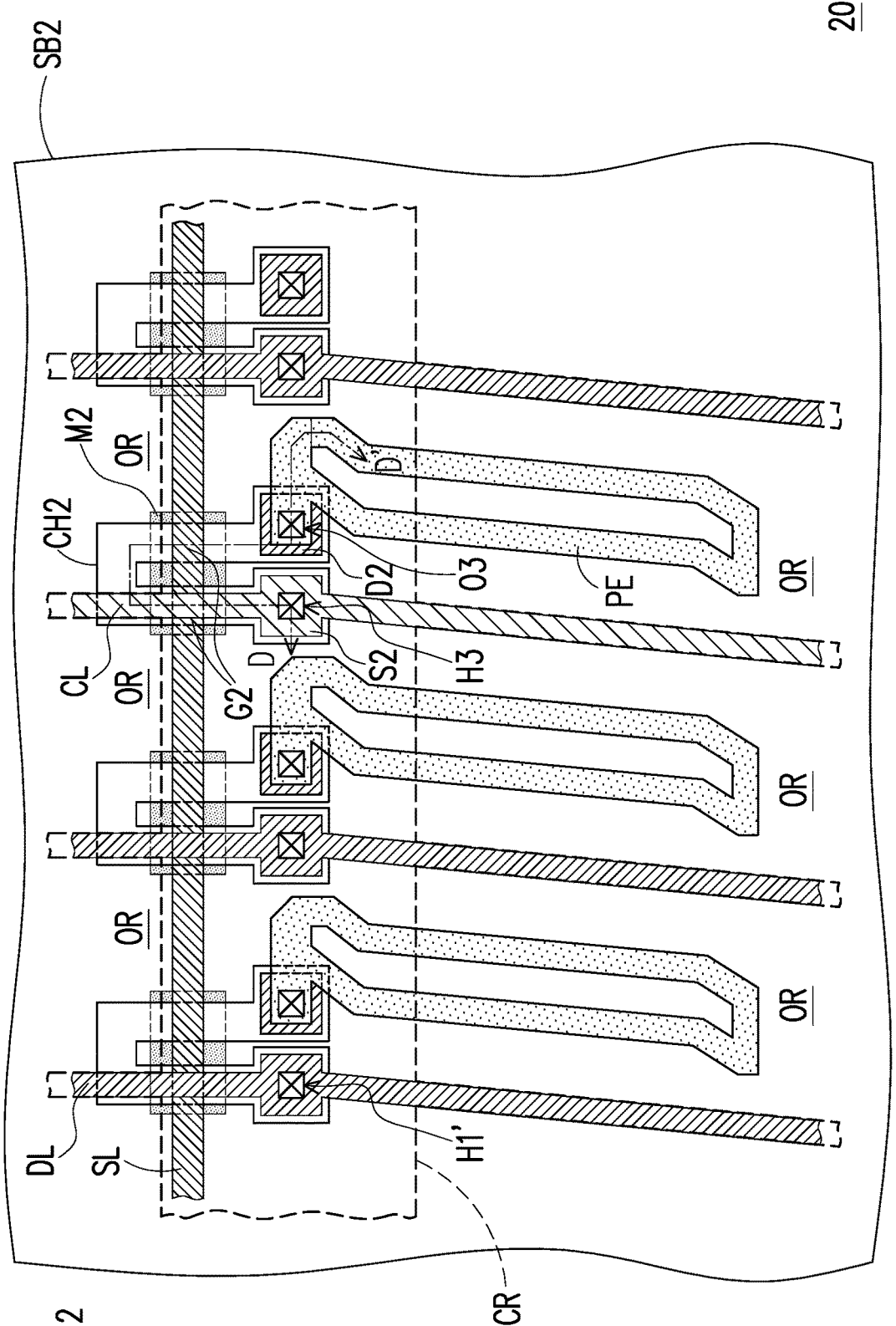
FIG. 4A is a schematic top view of a pixel array substrate of a display apparatus according to an embodiment of the disclosure.
Figure 5:
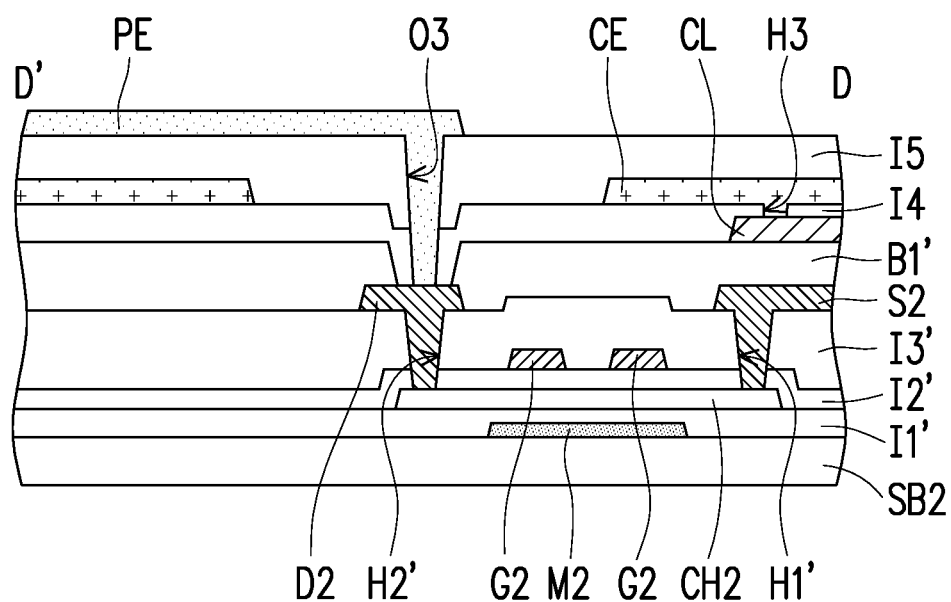
FIG. 5 is a schematic cross-sectional view of FIG. 4A taken along sectional line DD'.

FIG. 4A is a schematic top view of a pixel array substrate of a display apparatus according to an embodiment of the disclosure. For simplicity of explanation, FIG. 4A omits some components of the pixel array substrate 20. FIG. 5 is a schematic cross-sectional view of FIG. 4A taken along sectional line DD'.

Referring to FIG. 1, FIG. 4A and FIG. 5, the pixel array substrate 20 includes a second substrate SB2, a thin film transistor array AR, a plurality of pixel electrodes PE, and a common electrode CE.

The thin film transistor array AR, the pixel electrode PE, and the common electrode CE are disposed on the second substrate SB2. The thin film transistor array AR includes a plurality of switching elements T2, a plurality of scan lines SL, and a plurality of data lines DL.

The switching element T2 is, for example, disposed on the insulating layer I1'. In some embodiments, a light shielding layer M2 is interposed between the switching element T2 and the second substrate SB2. The switching element T2 includes a gate G2, a source S2, a drain D2, and a semiconductor channel layer CH2. The semiconductor channel layer CH2 is disposed on the insulating layer I1'. The gate G2 overlaps the semiconductor channel layer CH2, and an insulating layer I2' is interposed between the gate G2 and the semiconductor channel layer CH2. The gate G2 is electrically connected to the scan line SL. In the embodiment, the gate G2 and the scan line SL belong to the same conductive film layer, but the disclosure is not limited thereto. The insulating layer I3' is disposed on the insulating layer I2' and covers the gate G2 and the scan line SL. The source S2 and the drain D2 are disposed above the insulating layer I3', and the source S2 is electrically connected to the data line DL. In this embodiment, the source S2 and the data line DL belong to the same conductive film layer, but the disclosure is not limited thereto. The source S2 and the drain D2 are electrically connected to the semiconductor channel layer CH2 through the openings H1', H2' respectively, and the openings H1', H2' are disposed, for example, in the insulating layer I3' and the insulating layer I2'. The insulating layer B1' is disposed above the source S2 and the drain D2. The above-mentioned thin film transistor T2 is exemplified as a top gate type thin film transistor, but the disclosure is not limited thereto. According to other embodiments, the thin film transistor T2 described above may also be a bottom gate type thin film transistor.

Figure 4B:
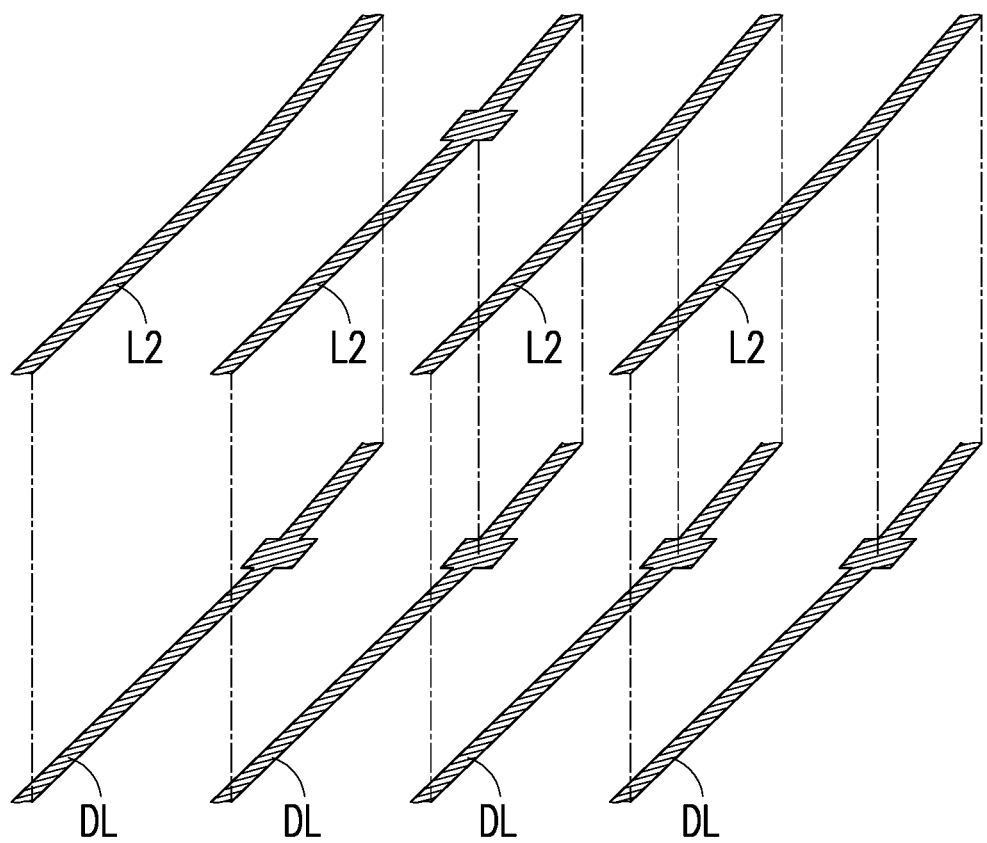
FIG. 4B is schematic side view of a second signal line and a data line according to an embodiment of the disclosure.

Please refer to FIG. 4B, in the embodiment, the second signal line L2 overlaps the data line DL in the direction (may also be referred to as the direction perpendicular to the second substrate SB2) perpendicular to the first substrate SB1, thereby improving the aperture ratio of the sensing display apparatus 1.

In the embodiment, the pixel array substrate 20 further includes a common electrode line CL. The common electrode line CL is disposed on the insulating layer B1'. In the embodiment, the extending direction of the common electrode line CL is the same as the extending direction of the data line DL. In some embodiments, the common electrode line CL overlaps the data line DL in the direction (may also be referred to as the direction perpendicular to the second substrate SB2) perpendicular to the first substrate SB1, thereby improving the aperture ratio of the sensing display apparatus 1.

The insulating layer I4 covers the common electrode line CL. The common electrode CE is disposed on the insulating layer I4, and is electrically connected to the common electrode line CL through the opening H3, and the opening H3 is disposed in the insulating layer I4. In some embodiments, the common electrode CE includes a touch electrode. In some embodiments, the common electrode CE and the shielding layer SM on the first substrate SB1 are electrically connected to the same signal source. It can also be that the same signal is applied to the common electrode CE and the shielding layer SM, thereby further improving the problem that the electric field generated by the sensing device substrate 20 affects the display quality.

The insulating layer I5 is disposed on the common electrode CE. The pixel electrode PE is disposed on the insulating layer I5, the pixel electrode PE overlaps the common electrode CE, and the pixel electrode PE is separated from the common electrode CE. The pixel electrode PE is electrically connected to the drain D2 of the thin film transistor T2 through the opening O3. In the embodiment, the opening O3 passes through the insulating layer B1', the insulating layer I4, the insulating layer I5, and the common electrode CE, but the disclosure is not limited thereto. In some embodiments, the pixel array substrate 20 may drive liquid crystals using Fringe Field Switching (FFS) technology or In-Plane-Switching (IPS) technology.

Referring to FIG. 1, the display apparatus 1 may further include a backlight module BL. The backlight module BL is disposed under the pixel array substrate 20, and it may be that the pixel array substrate 20 is disposed between the backlight module BL and the sensing device substrate 10. When a finger F approaches the sensing device substrate 10, the light LR emitted by the backlight module BL is reflected by the finger F to the photo-sensitive layer R.

Figure 6:
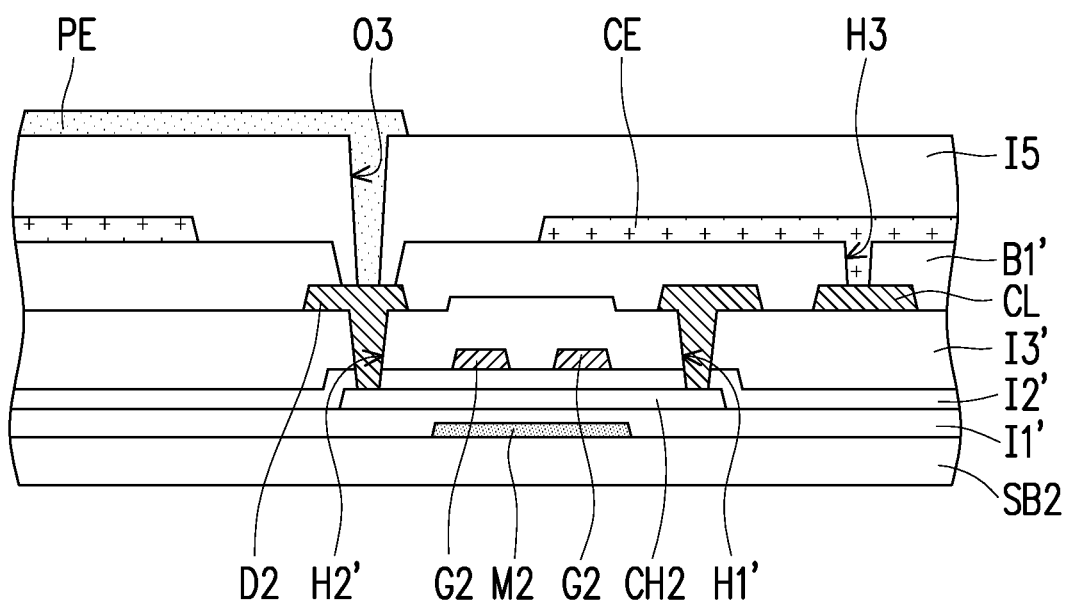
FIG. 6 is a schematic cross-sectional view of a pixel array substrate of a display apparatus according to an embodiment of the disclosure.

FIG. 6 is a schematic cross-sectional view of a pixel array substrate of a display apparatus according to an embodiment of the disclosure. It is to be explained that, the embodiment of FIG. 6 has adopted component notations and part of the contents from the embodiment of FIG. 5, wherein the same notations are used for representing the same or similar components, and descriptions of the same technical contents are omitted. The descriptions regarding the omitted part may be referred to the previous embodiments, and thus are not repeated herein.

Referring to FIG. 6, in the embodiment, the common electrode line CL of the pixel array substrate 20a is disposed on the insulating layer I3'. In the embodiment, the common electrode line CL and the data line DL belong to the same conductive film layer, and the common electrode line CL and the data line DL extend in the same direction.

The insulating layer B1' covers the common electrode line CL, the data line DL, the source S2, and the drain D2. The common electrode CE is disposed on the insulating layer B1', and is electrically connected to the common electrode line CL through the opening H3, and the opening H3 is disposed in the insulating layer B1'.

By using the same process to form the common electrode line CL, the data line DL, the source S2, and the drain D2, the number of masks required in the manufacturing process may be saved.

Figure 7:
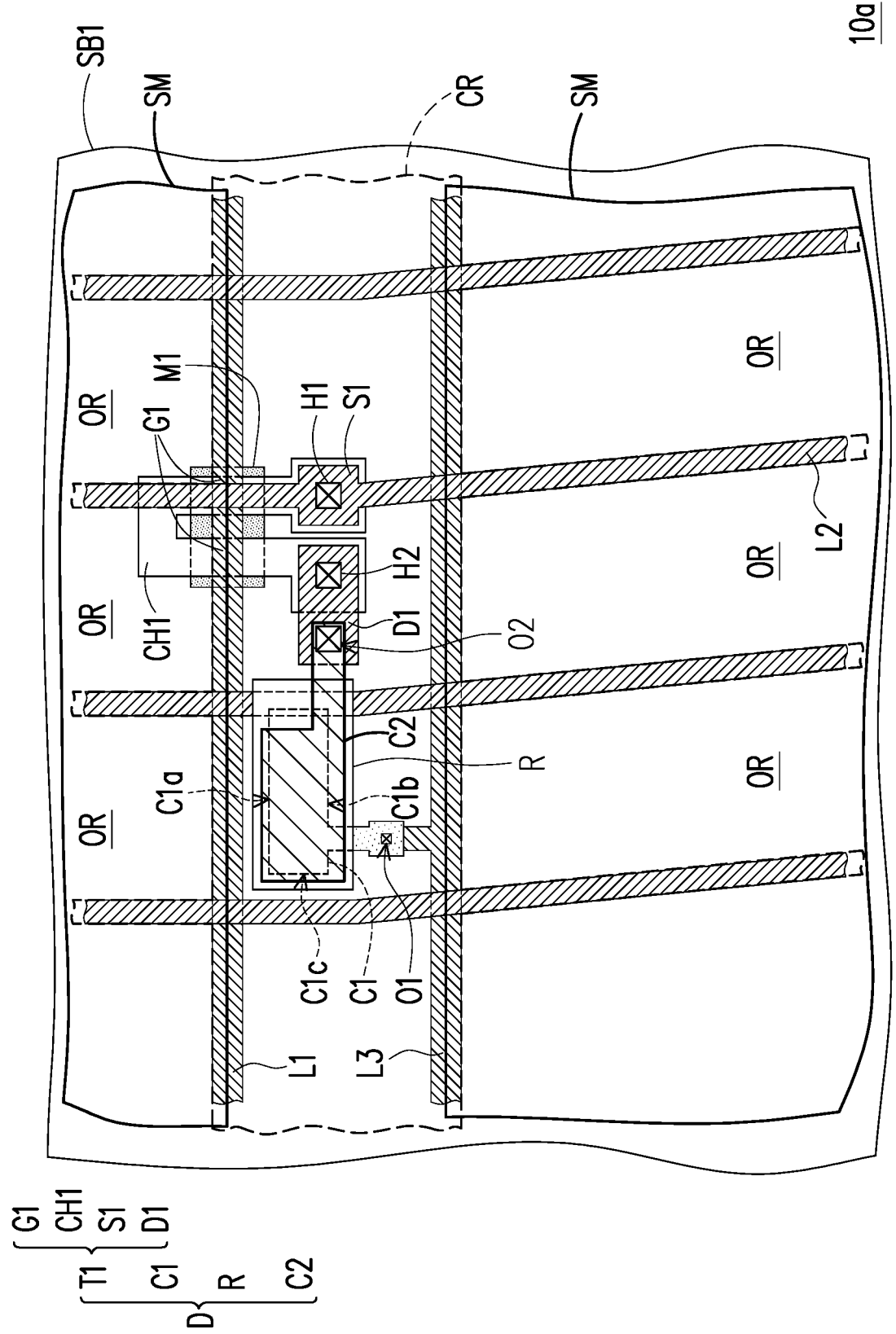
FIG. 7 is a schematic bottom view of a sensing device substrate of a display apparatus according to an embodiment of the disclosure.

FIG. 7 is a schematic bottom view of a sensing device substrate of a display apparatus according to an embodiment of the disclosure. It is to be explained that, the embodiment of FIG. 7 has adopted component notations and part of the contents from the embodiments of FIG. 2 to FIG. 3C, wherein the same notations are used for representing the same or similar components, and descriptions of the same technical contents are omitted. The descriptions regarding the omitted part may be referred to the previous embodiments, and thus are not repeated herein.

Referring to FIG. 7, in the embodiment, the shielding layer SM covers the entire light transmitting region OR. The problem that the electric field generated by the sensing device substrate 10a affects the liquid crystal molecules in the display medium layer LC is improved by the shielding layer SM, and the display quality of the display apparatus 1 may be improved.

In this embodiment, the common electrode CE in the pixel array substrate corresponding to the sensing device substrate 10a is not used as the touch electrode. Therefore, it is not necessary to take into consideration the problem that the touch function is affected due to that the shielding layer SM covers the entire light transmitting region OR.

Figure 8:
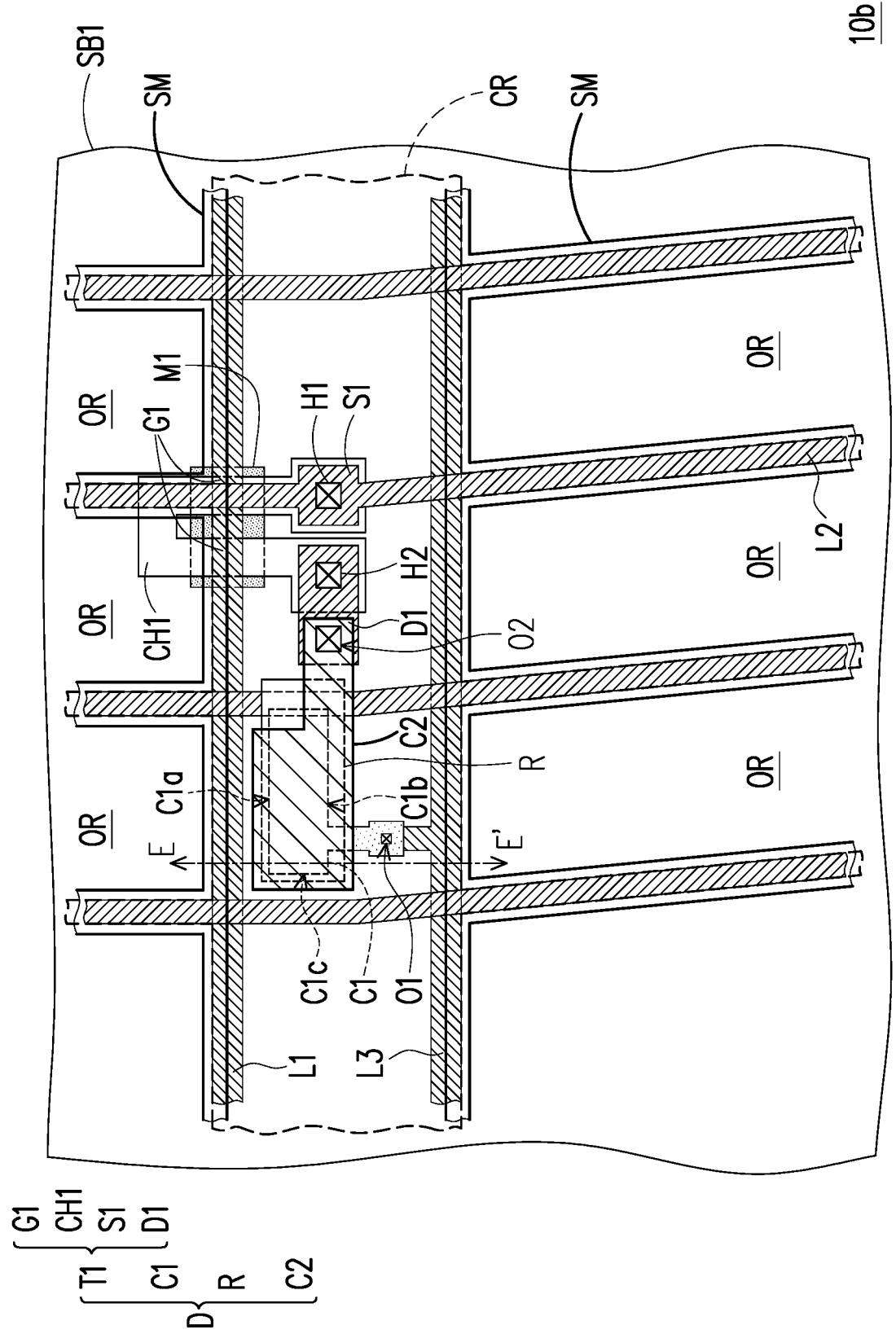
FIG. 8 is a schematic bottom view of a sensing device substrate of a display apparatus according to an embodiment of the disclosure.
Figure 9:
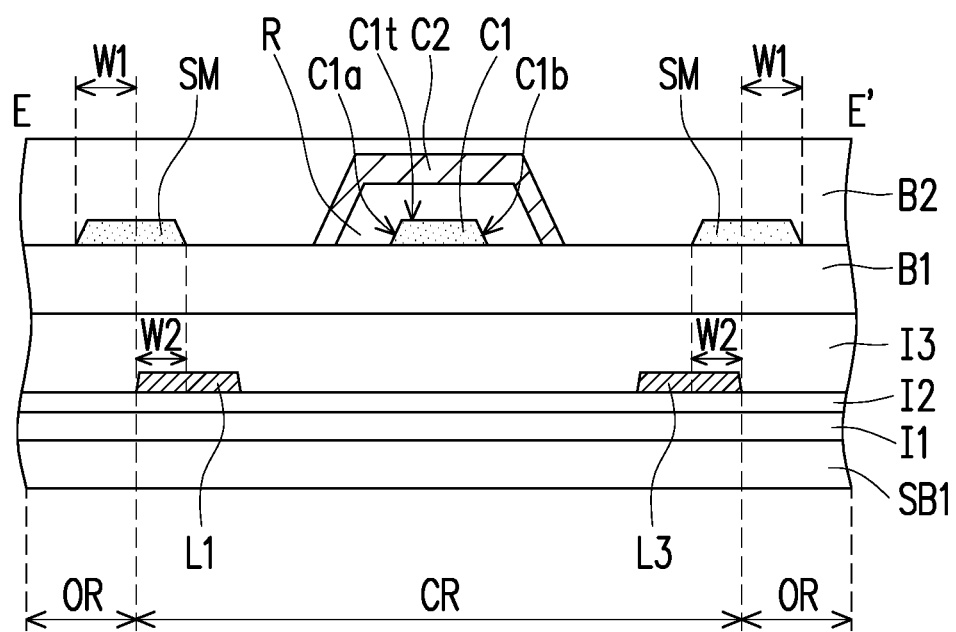
FIG. 9 is a schematic cross-sectional view of FIG. 8 taken along sectional line EE'.

FIG. 8 is a schematic bottom view of a sensing device substrate of a display apparatus according to an embodiment of the disclosure. FIG. 9 is a schematic cross-sectional view of FIG. 8 taken along sectional line EE'. It is to be explained that, the embodiments of FIG. 8 and FIG. 9 have adopted component notations and part of the contents from the embodiments of FIG. 2 to FIG. 3C, wherein the same notations are used for representing the same or similar components, and descriptions of the same technical contents are omitted. The descriptions regarding the omitted part may be referred to the previous embodiments, and thus are not repeated herein.

Referring to FIG. 8 and FIG. 9, in the embodiment, the photo-sensitive layer R is disposed between the top surface C t of the electrically conductive layer C1 and the electrode layer C2, between the first side surface C1a of the electrically conductive layer C1 and the electrode layer C2, and between the second side C1b of the electrically conductive layer C1 and the electrode layer C2. In this embodiment, the photo-sensitive layer R is further disposed between the third side surface C1c of the electrically conductive layer C1 and the electrode layer C2. The electrode layer C2 is farther from the first substrate SB1 than the electrically conductive layer C1. The electrode layer C2 is closer to the pixel array substrate 20 than the electrically conductive layer C1.

In this embodiment, the side photosensitive area of the photo-sensitive layer R may be increased, thereby increasing the ratio of the photocurrent to the dark current when the sensing device substrate 10*b* senses the object, and improving the problem that the sensing device substrate 10*b* is insufficient in sensitivity.

Figure 10A:
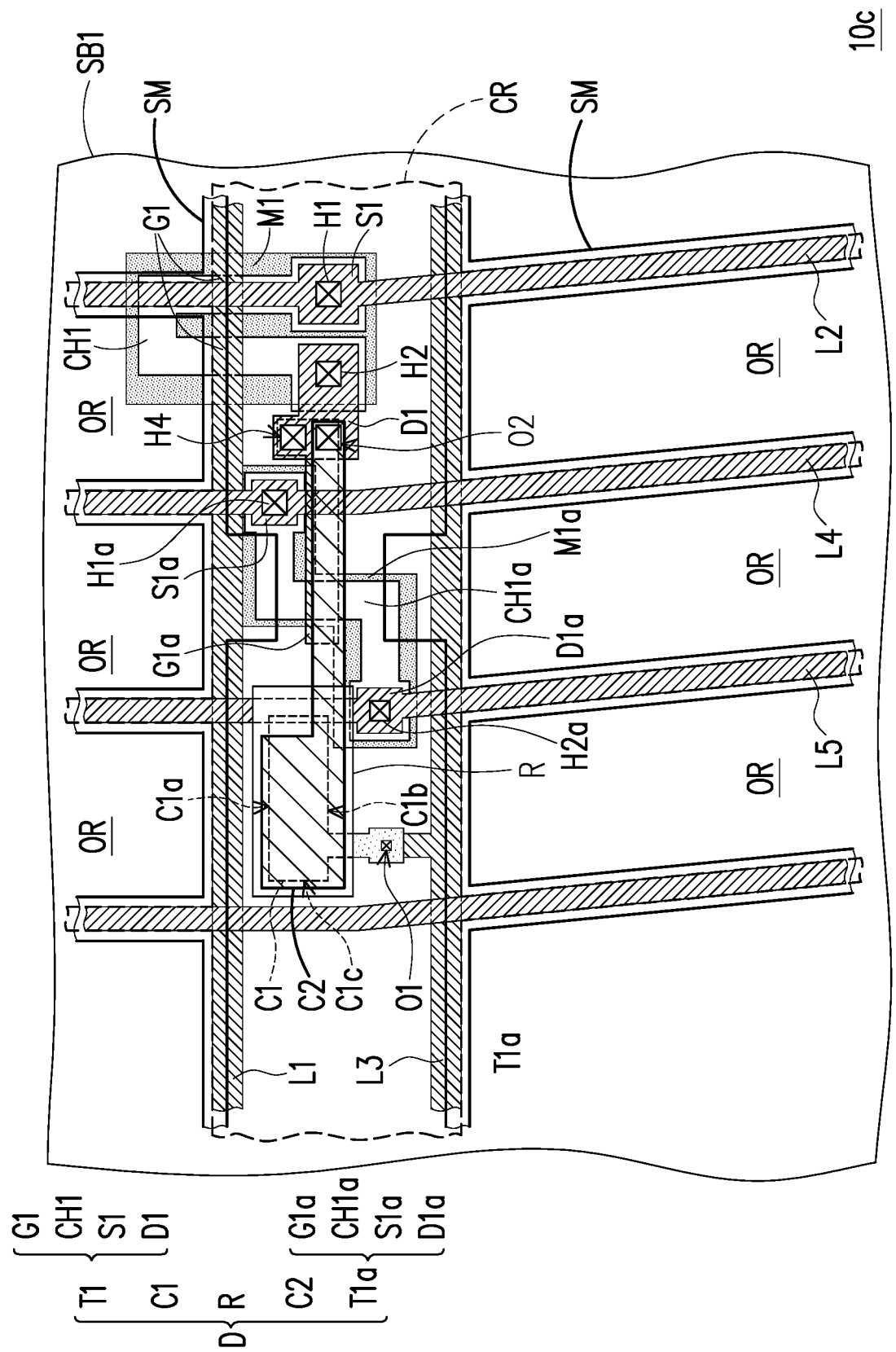
FIG. 10A is a schematic bottom view of a sensing device substrate of a display apparatus according to an embodiment of the disclosure.
Figure 10B:
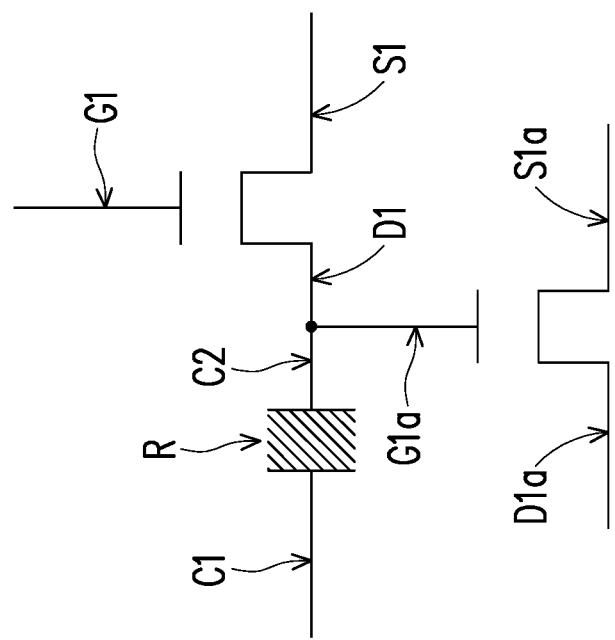
FIG. 10B is a circuit diagram of the sensing device substrate in FIG. 10A.

FIG. 10A is a schematic bottom view of a sensing device substrate of a display apparatus according to an embodiment of the disclosure. FIG. 10B is a circuit diagram of the sensing device substrate in FIG. 10A.

Referring to FIG. 10A and FIG. 10B, the sensing device D of the sensing device substrate 10*c* includes the switching element T1, a switching element T1*a*, the electrically conductive layer C1, the photo-sensitive layer R, and the electrode layer C2.

The switching element T1*a* includes a gate G1*a*, a source S1*a*, a drain D1*a*, and a semiconductor channel layer CH1*a*. In the embodiment, a light shielding layer M1*a* is further included between the switching element T1*a* and the first substrate SB1, but the disclosure is not limited thereto.

The gate G1*a* overlaps the semiconductor channel layer CH1*a*. The gate G1*a* is electrically connected to the switching element T1 and the electrode layer C2. For example, the drain D1 of the switching element T1 is electrically connected to the gate G1*a* through the opening H4, and the electrode layer C2 is electrically connected to the gate G1*a* through the drain D1. In this embodiment, the gate G1*a*, the first signal line L1 and the third signal line L3 belong to the same conductive film layer, but the disclosure is not limited thereto. The source S1*a* is electrically connected to the fourth signal line L4. In some embodiments, the second signal line L2 is electrically connected to the signal VSS, and the fourth signal line L4 is electrically connected to the signal VDD. The drain D1*a* is electrically connected to the fifth signal line L5. In this embodiment, the source S1*a*, the drain D1*a*, the second signal line L2, the fourth signal line L4, and the fifth signal line L5 belong to the same conductive film layer, but the disclosure is not limited thereto. The source S1*a* and the drain D1*a* are electrically connected to the semiconductor channel layer CH1*a* through the openings H1*a* and H2*a* respectively, and such design allows the signal to be improved. The above-described switching element T1*a* is exemplified as a top gate type thin film transistor, but the disclosure is not limited thereto. According to other embodiments, the above-mentioned switching element T1*a* may also be a bottom gate type thin film transistor or other suitable thin film transistors.

In this embodiment, a portion of the shielding layer SM extends toward the position of the switching element T1*a*, which further improves the problem that the electric field generated by the sensing device substrate 10*c* affects the liquid crystal molecules in the display medium layer LC.

Figure 11A:
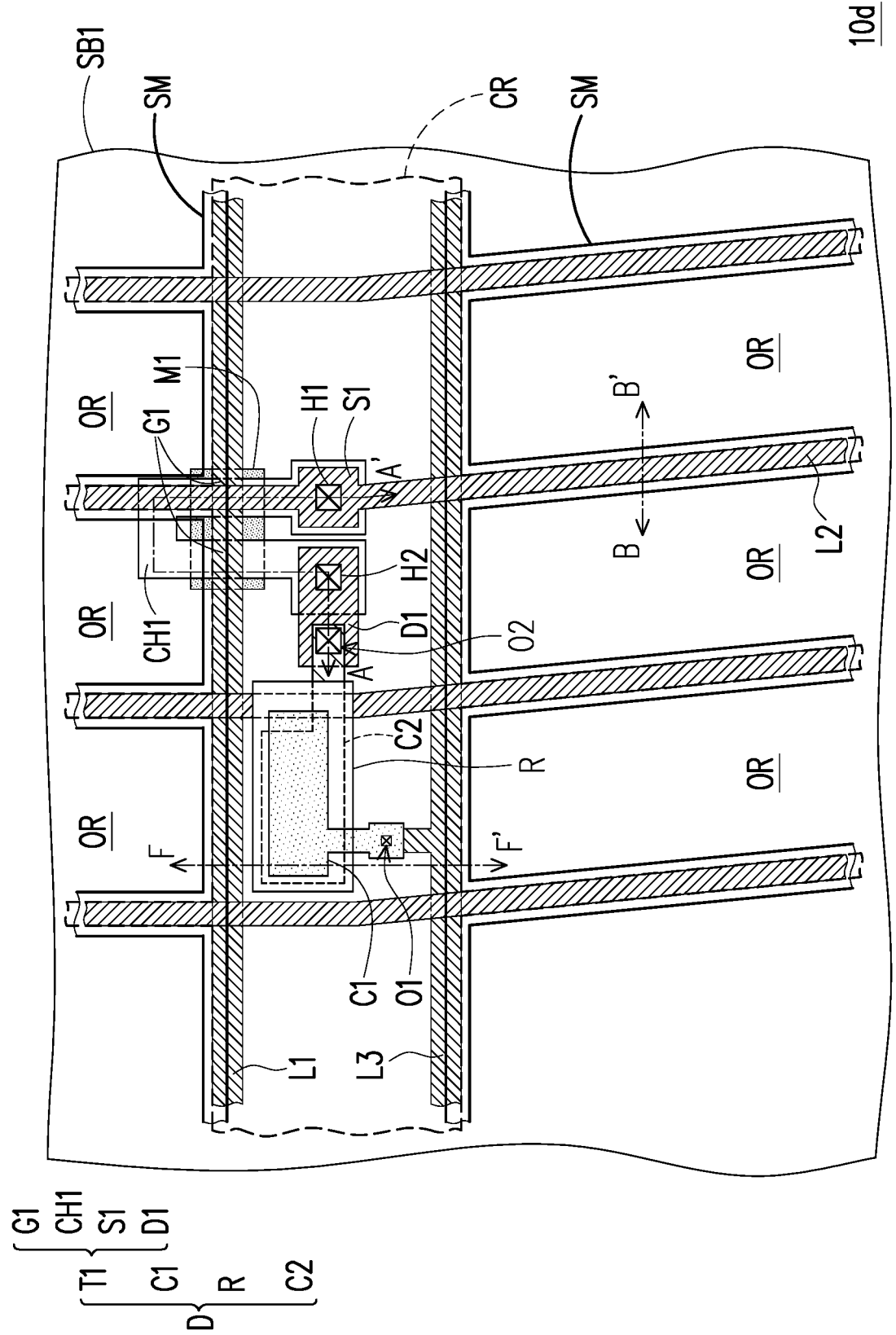
FIG. 11A is a schematic bottom view of a sensing device substrate of a display apparatus according to an embodiment of the disclosure.
Figure 11B:
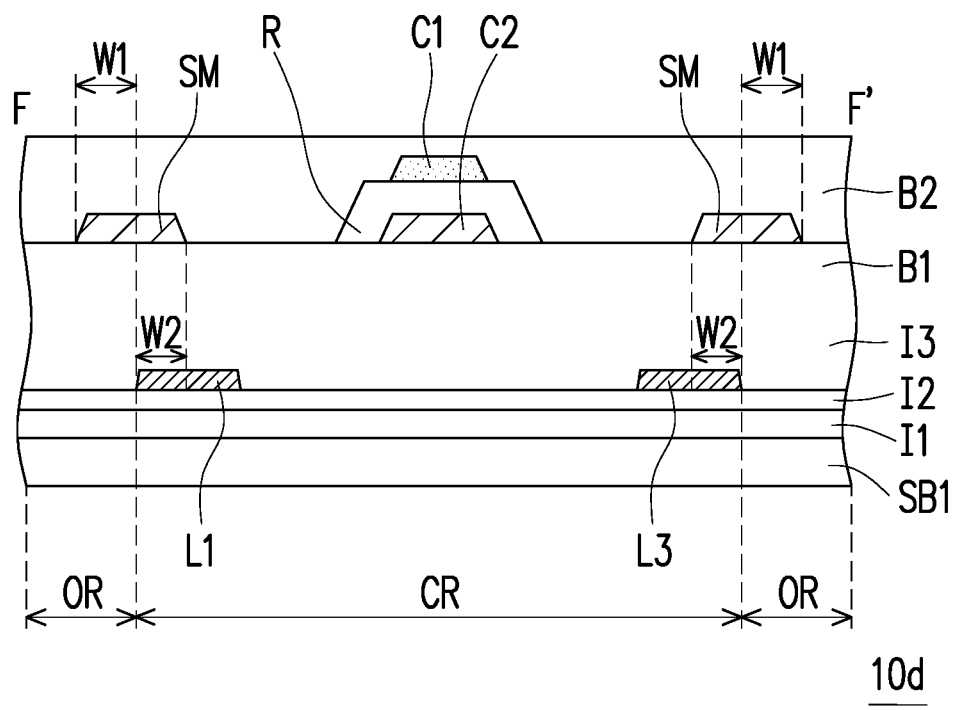
FIG. 11B is a schematic cross-sectional view of FIG. 11A taken along sectional line FF'.

FIG. 11A is a schematic bottom view of a sensing device substrate of a display apparatus according to an embodiment of the disclosure. FIG. 11B is a schematic cross-sectional view of FIG. 11A taken along sectional line FF'. It should be noted that the embodiments of FIG. 11A and FIG. 11B adopt the reference numerals and some content mentioned in the embodiments of FIG. 2-FIG. 3C, wherein the same or similar elements are denoted by the same or similar reference numerals, and the same technical content is omitted. The omitted content may be derived from the above embodiments and thus not repeated herein.

Referring to FIG. 11A and FIG. 11B, in the embodiment, the electrically conductive layer C1 of the sensing device substrate 10*d* is closer to the pixel array substrate than the electrode layer C2.

In the embodiment, the electrode layer C2 is electrically connected to the switching element T1. The material of the electrode layer C2 is preferably a transparent conductive material such as indium tin oxide, indium zinc oxide, aluminum tin oxide, aluminum zinc oxide, indium gallium zinc oxide or other suitable oxide or a stacked layer of at least two of the above. In the embodiment, the shielding layer SM and the electrode layer C2 are the same conductive film layer.

The material of the electrically conductive layer C1 is, for example, a stack of molybdenum, aluminum, titanium, copper, gold, silver or other conductive material or a combination of two or more of the above. In some embodiments, the electrode layer C1 may be used as a reflective layer, thereby increasing the light that can be received by the photo-sensitive layer R.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A sensing display apparatus, comprising:
   a pixel array substrate; and
   a sensing device substrate, facing the pixel array substrate, and comprising:
   a first substrate;
   a sensing device, disposed on the first substrate;
   a first signal line, a second signal line, and a third signal line, disposed on e first substrate, wherein the sensing device comprises:
      a first switching element, electrically connected to the first signal line and the second signal line;
      an electrically conductive layer, electrically connected to the third signal line;
      an electrode layer, electrically connected to the first switching element; and
      a photo-sensitive layer, disposed between the electrode layer and the electrically conductive layer;
   an electric field shielding layer, disposed between the first signal line and the pixel array substrate, between the second signal line and the pixel array substrate, and between the third signal line and the pixel array substrate, wherein the sensing display apparatus has a plurality of light transmitting regions and a light shielding region surrounding the light transmitting regions, the sensing device, the first signal line, the second signal line and the third signal are disposed in the light shielding region, wherein the electric field shielding layer comprises a conductive material; and
   a display medium layer, disposed between the pixel array substrate and the sensing device substrate.

2. The sensing display apparatus according to claim 1, wherein the display medium layer comprises a negative liquid crystal.

3. The sensing display apparatus according to claim 1, wherein the pixel array substrate comprises:
   a second substrate;
   a thin film transistor array, disposed on the second substrate;
   a plurality of pixel electrodes, electrically connected to the thin film transistor array; and
   a common electrode, disposed on the second substrate.

4. The sensing display apparatus according to claim 3, wherein the common electrode comprises a touch electrode.

5. The sensing display apparatus according to claim 3, wherein the common electrode and the electric field shielding layer are electrically connected to the same signal source.

6. The sensing display apparatus according to claim 1, wherein a width of the electric field shielding layer extending from the light shielding region into the light transmitting regions is greater than or equal to 1.5 µm.

7. The sensing display apparatus according to claim 1, wherein the electric field shielding layer covers the entire light transmitting regions.

8. The sensing display apparatus according to claim 1, wherein:
the photo-sensitive layer covers a top surface of the electrically conductive layer, a first side surface of the electrically conductive layer, and a second side surface of the electrically conductive layer, and the electrode layer is closer to the pixel array substrate than the electrically conductive layer.

9. The sensing display apparatus according to claim 8, wherein the electric field shielding layer and the electrically conductive layer are the same conductive film layer.

10. The sensing display apparatus according to claim 8, wherein the photo-sensitive layer is disposed between the top surface of the electrically conductive layer and the electrode layer, between the first side surface of the electrically conductive layer and the electrode layer, and between the second side surface of the electrically conductive layer and the electrode layer.

11. The sensing display apparatus according to claim 8, wherein the sensing device further comprises a second switching element, a gate of the second switching element electrically connected to a drain of the first switching element and the electrode layer.

12. The sensing display apparatus according to claim 1, wherein the sensing device is disposed between the third signal line and the first signal line, a portion of the first signal line and a portion of the third signal line do not overlap the electric field shielding layer, and the portion of the first signal line not overlapping the electric field shielding layer is closer to the electrically conductive layer than a portion of the first signal line overlapping the electric field shielding layer, the portion of the third signal line not overlapping the electric field shielding layer is closer to the electrically conductive layer than a portion of the third signal line overlapping the electric field shielding layer.

13. A sensing display apparatus, comprising:
a pixel array substrate;
a sensing device substrate, facing the pixel array substrate;
a display medium layer, disposed between the pixel array substrate and the sensing device substrate, and the sensing device substrate comprising:
a first substrate;
a sensing device, disposed on the first substrate;
a first signal line, a second signal line, and a third signal line, disposed on the first substrate, wherein the sensing device comprises:
a first switching element, electrically connected to the first signal line and the second signal line;
an electrically conductive layer, electrically connected to the third signal line;
an electrode layer, electrically connected to the first switching element; and
a photo-sensitive layer, disposed between the electrode layer and the electrically conductive layer; and
an electric field shielding layer, disposed between the first signal line and the pixel array substrate, between the second signal line and the pixel array substrate, and between the third signal line and the pixel array substrate, wherein the electric field shielding layer comprises a conductive material.

14. The sensing display apparatus according to claim 13, wherein the display medium layer comprises a negative liquid crystal.

15. The sensing display apparatus according to claim 13, wherein the pixel array substrate comprises:
a second substrate;
a thin film transistor array, disposed on the second substrate;
a plurality of pixel electrodes, electrically connected to the thin film transistor array; and
a common electrode, disposed on the second substrate, wherein the common electrode comprises a touch electrode.

16. The sensing display apparatus according to claim 13, wherein the sensing display apparatus has a plurality of light transmitting regions and a light shielding region surrounding the light transmitting regions, a width of the electric field shielding layer extending from the light shielding region into the light transmitting regions is greater than or equal to 1.5 µm.

17. The sensing display apparatus according to claim 13, wherein the sensing display apparatus has a plurality of light transmitting regions and a light shielding region surrounding the light transmitting regions, wherein the electric field shielding layer covers the entire light transmitting regions.

18. The sensing display apparatus according to claim 13, wherein the electric field shielding layer and the electrically conductive layer are the same conductive film layer.

19. The sensing display apparatus according to claim 13, wherein the photo-sensitive layer is disposed between a top surface of the electrically conductive layer and the electrode layer, between a first side surface of the electrically conductive layer and the electrode layer, and between a second side surface of the electrically conductive layer and the electrode layer.

20. The sensing display apparatus according to claim 13, wherein the sensing device further comprises a second switching element, a gate of the second switching element electrically connected to a drain of the first switching element and the electrode layer.

* * * * *